US00PP21822P3

(12) United States Plant Patent
Portman

(10) Patent No.: US PP21,822 P3
(45) Date of Patent: Mar. 29, 2011

(54) ***PITTOSPORUM* PLANT NAMED 'ELFIN'**

(50) Latin Name: *Pittosporum tenuifolium*
Varietal Denomination: Elfin

(76) Inventor: Faye Portman, Carterton (NZ)

( * ) Notice: Subject to any disclaimer, the term of this patent is extended or adjusted under 35 U.S.C. 154(b) by 226 days.

(21) Appl. No.: 12/283,162

(22) Filed: Sep. 10, 2008

(65) Prior Publication Data

US 2009/0083887 P1 Mar. 26, 2009

(30) Foreign Application Priority Data

Sep. 20, 2007 (NZ) ..... SHM229

(51) Int. Cl.
*A01H 5/00* (2006.01)

(52) U.S. Cl. ..... Plt./234

(58) Field of Classification Search ..... Plt./234
See application file for complete search history.

(56) References Cited

U.S. PATENT DOCUMENTS

PP15,329 P2 * 11/2004 Fyfe ..... Plt./234

OTHER PUBLICATIONS

Winter, Garth "Pittosporum 'Elfin'" Irises and Archives Blog Jul. 31, 2006 available at: http://irisarchives.blogspot.com/2006/07/pittosporum-ellfin.html.*

Blogger user profile, Gareth Winter available at: http://www.blogger.com/profile/03578356462912887749.*

* cited by examiner

*Primary Examiner*—Wendy Haas
(74) *Attorney, Agent, or Firm*—Mark P. Bourgeois

(57) ABSTRACT

A new cultivar of *Pittosporum* plant named 'Elfin' that is characterized by a small overall size, short light green leaves and a short crop time.

1 Drawing Sheet

Botanical classification: *Pittosporum tenuifolium.*

Variety denomination: 'Elfin'.

BACKGROUND OF THE INVENTION

The present invention relates to a new and distinct cultivar of *Pittosporum* plant botanically known as *Pittosporum tenuifolium* and hereinafter referred to by the cultivar name 'Elfin'.

The new cultivar was discovered in a cultivated area of Carterton, New Zealand in 2001. 'Elfin' was discovered as a naturally occurring branch mutation of an unnamed *Pittosporum tenuifolium* plant that was growing in an outdoor garden.

Asexual reproduction by tip cuttings of the new cultivar 'Elfin' was first performed in 2001 in Carterton, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pittosporum* cultivar 'Elfin'.

1. *Pittosporum* 'Elfin' exhibits a small overall size.
2. *Pittosporum* 'Elfin' exhibits short leaves.
3. *Pittosporum* 'Elfin' exhibits light green leaves.
4. *Pittosporum* 'Elfin' exhibits a short crop time.

The new cultivar 'Elfin' is distinguishable from the parent plant by the following characteristics:

1. 'Elfin' has a dwarf habit and small overall size of 0.6 meters in height and 0.6 meters in width. The parent plant grows to 10 meters in height and 10 meters in width.
2. 'Elfin' has shorter leaves than the parent plant. The leaves of 'Elfin' are 15 mm. in length. The leaves of the parent plant are 40 mm. in length.
3. 'Elfin' has lighter green leaves than the parent plant.
4. 'Elfin' exhibits a shorter crop time than the parent plant.

The closest comparison cultivars are *Pittosporum* 'Golf Ball' (U.S. Plant Pat. No. 15,329) and 'Mountain Green' (not patented).

The new cultivar 'Elfin' is distinguishable from 'Golf Ball' by the following characteristics:

1. 'Elfin' has shorter leaves. The leaves of 'Elfin' are 15 mm. in length. The leaves of 'Golf Ball' are 22 mm. in length.
2. 'Elfin' has leaves that are lighter green than the leaves of 'Golf Ball'.

The new cultivar 'Elfin' is distinguishable from 'Mountain Green' by the following characteristics:

1. 'Elfin' has a smaller overall size. 'Elfin' grows to 0.6 meters in height and 0.6 meters in width. 'Mountain Green' grows to 8 meters in height and 8 meters in width.
2. 'Elfin' has shorter leaves. The leaves of 'Elfin' are 15 mm. in length. The leaves of 'Mountain Green' are 30 mm. in length.
3. 'Elfin' has leaves that are lighter green than the leaves of 'Mountain Green'.

BRIEF DESCRIPTION OF THE DRAWING

The accompanying photograph illustrates the distinguishing traits of *Pittosporum* 'Elfin'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Pittosporum* cultivar named 'Elfin'. Data was collected in Auckland, New Zealand from 24 month old outdoor grown plants in 3.0 liter containers. The time of year was Winter in the Southern Hemisphere and the average temperature range was 12 to 18 degrees Centigrade during the day and 4 to 11 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Elfin' has not been tested under all possible conditions and phenotypic differences may be observed with variations in environmental, climatic, and cultural conditions, however, without any variance in genotype.

Botanical classification: *Pittosporum tenuifolium* 'Elfin'.

Use: Ornamental perennial shrub.

Parentage: 'Elfin' is a naturally occurring branch mutation of an unnamed *Pittosporum tenuifolium* plant.

Vigor: Moderate.

Growth rate: 0.2 m. per year.

Crop time: 8 weeks.

Plant shape: Rounded.

Growth habit: Dense, bushy habit.

Hardiness: Tolerant to low temperatures of −7 degrees Centigrade and high temperatures of +30 degrees Centigrade.

Suitable container size: 2 liter container.

Height: Average 0.6 m in height.

Width: Average 0.6 m in width.

Propagation: Tip cuttings.

Root system: Fine and fibrous.

Stem:

*Branching habit.*—Basal branching.

*Lateral branches.*—Quantity: Approximately 35. Length: Average 0.2 m. Diameter: Average 1 mm. Internode length: 3 mm. Color: 200A. Strength: Strong. Shape: Round. Pubescence: Absent. Pinching: Yes.

Foliage:

*Texture.*—Leathery.

*Leaf arrangement.*—Alternate.

*Compound or single.*—Single.

*Leaf shape.*—Elliptic.

*Leaf apex.*—Apiculate.

*Leaf base.*—Acute.

*Leaf length.*—Average 15 mm. in length.

*Leaf width.*—9 mm. in width.

*Quantity of leaves per lateral branch.*—Average 36.

*Pubescence.*—Absent.

*Leaf margin.*—Entire.

*Young leaf color* (*upper surface*).—145A.

*Young leaf color* (*lower surface*).—145C.

*Mature leaf color* (*upper surface*).—145A.

*Mature leaf color* (*lower surface*).—145C.

*Vein color* (*upper surface*).—N144A.

*Vein color* (*lower surface*).—N145A.

*Petiole length.*—3 mm.

*Petiole diameter.*—1 mm.

*Petiole color.*—N144A.

*Durability of foliage to stress.*—Moderate to high.

Flowers: Flowers have not been observed growing on 'Elfin'.

Disease and insect resistance: Plants of the new *Pittosporum* have not been observed for disease or insect resistance.

The invention claimed is:

1. A new and distinct variety of *Pittosporum* plant named 'Elfin' as described and illustrated.

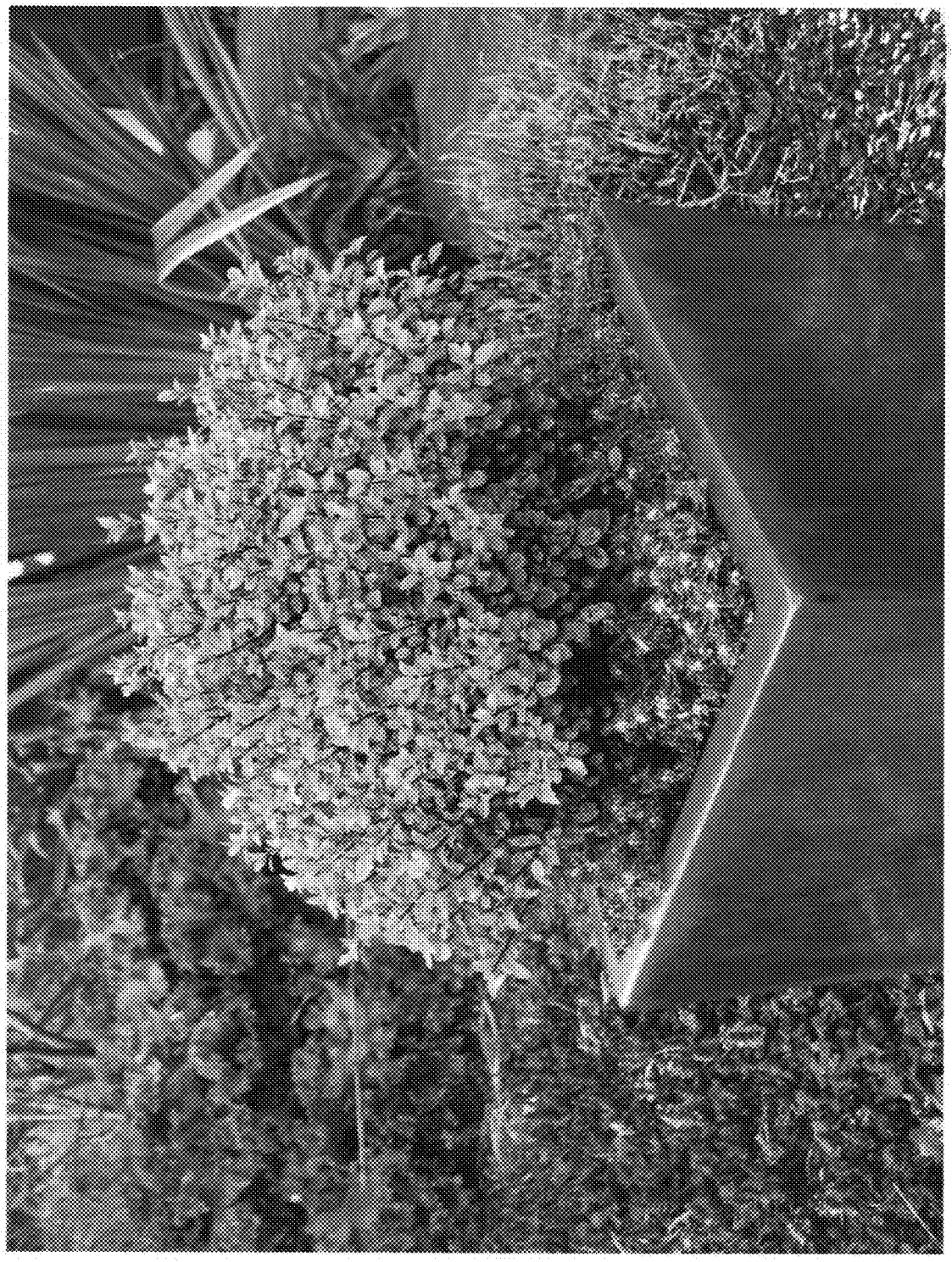

* * * * *